United States Patent [19]

Tomlin et al.

[11] 4,063,926

[45] Dec. 20, 1977

[54] HERBICIDAL METHODS AND COMPOSITIONS USING 3,5-DICHLORO-2,6-DIFLUORO-4-HYDROXYPYRIDINE OR SALTS THEREOF

[75] Inventors: Clive Dudley Spencer Tomlin, Maidenhead; John Walter Slater, March; David Hartley, Bishop's Stortford, all of England

[73] Assignee: Imperial Chemical Industries Limited, London, England

[21] Appl. No.: 258,627

[22] Filed: June 1, 1972

Related U.S. Application Data

[63] Continuation of Ser. No. 761,850, Sept. 23, 1968, abandoned, which is a continuation-in-part of Ser. No. 571,701, Aug. 11, 1966, abandoned.

[30] Foreign Application Priority Data

Aug. 19, 1965 United Kingdom ............... 35596/65

[51] Int. Cl.$^2$ ............................................... A01N 9/22
[52] U.S. Cl. ............................................ 71/94; 71/86; 71/87; 424/200; 424/263; 260/290 HL
[58] Field of Search ............................................ 71/94

[56] References Cited

U.S. PATENT DOCUMENTS

| 3,244,722 | 4/1966 | Johnston et al. | 71/94 |
| 3,249,419 | 5/1966 | Martin | 71/94 |
| 3,296,272 | 1/1967 | Johnston | 424/263 |
| 3,317,542 | 5/1967 | Hazeldine et al. | 71/94 |
| 3,364,223 | 1/1968 | Johnston | 71/94 |
| 3,438,993 | 4/1969 | Wilbert et al. | 71/94 |

FOREIGN PATENT DOCUMENTS

1,161,491 8/1969 United Kingdom ..................... 71/94

OTHER PUBLICATIONS

Chambers et al., "Polyfluoro Heterocyclic Cmpds. etc."; (1964) CA63, pp. 1764–1765, (1965).
*Journal of The Chemical Society,* Supplement I, 1964, pp. 5634–5640.

*Primary Examiner*—Glennon H. Hollrah
*Attorney, Agent, or Firm*—Cushman, Darby & Cushman

[57] ABSTRACT

Herbicidal formulations are provided utilizing as active ingredient, 4-hydroxy-2,3,5,6-tetrahalopyridines and salts thereof.

2 Claims, No Drawings

HERBICIDAL METHODS AND COMPOSITIONS USING 3,5-DICHLORO-2,6-DIFLUORO-4-HYDROXYPYRIDINE OR SALTS THEREOF

This is a continuation of application Ser. No. 761,850, filed Sept. 23, 1968, now abandoned, said application Ser. No. 761,850 being a continuation-in-part of Ser. No. 571,701, filed Aug. 11, 1966, now abandoned.

This invention relates to agriculturally-useful compositions comprising a fluoropyridine compound as active ingredient and to new fluoropyridines and processes for their preparation. More particularly this invention relates to herbicidal compositions comprising a fluoropyridine compound as the active ingredient.

The invention provides agriculturally-useful compositions comprising as an active ingredient a fluoropyridine compound having the general formula:

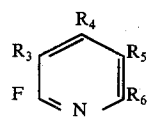

where $R_3$ and $R_5$, which may be the same or different, are atoms of fluorine or chlorine and either a. $R_6$ is an atom of fluorine or chlorine and $R_4$ is an hydroxyl group, an acyloxy group or an acylthio group, or b. $R_4$ is an atom of fluorine or chlorine and $R_6$ is an hydroxyl group, or a salt of any of the foregoing compounds wherein $R_4$ or $R_6$ is an hydroxyl group, together with a carrier for the active ingredient comprising a solid diluent, or a liquid diluent containing a surface active agent.

The term "acyl", where used in this specification, is intended to include the groups —CO.X, —SO$_2$.X and

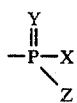

where Y is oxygen or sulphur and X and Z are monovalent groups.

In the present specification the fluorine atom has been designated as being in the 2-position although it is recognised that under alternative nomenclature it may often be designated as being in the 6-position.

In particular, $R_4$ may be an —S.CO.X, —O.CO.X, —O.SO$_2$.X, or —S.SO$_2$.X group where X is an unsubstituted or substituted alkyl or an alryl radical; where X is an alkyl radical or a substituted alkyl radical it is preferably one containing from one to twelve carbon atoms and when X is an aryl radical it is preferably an unsubstituted phenyl radical or a phenyl radical substituted with one or more halogen, nitro, alkyl or alkoxy groups.

Other preferred compositions according to the invention comprise as an active ingredient a fluoropyridine compound, or a salt thereof, of the above general formula in which $R_4$ or $R_6$, and especially $R_4$, is a hydroxyl group.

When the composition comprises a salt of a compound wherein $R_4$ or $R_6$ is an hydroxyl group the salt may be derived from the wide variety of organic or inorganic bases. It is preferred that the salt be a water-soluble salt. Suitable salts include alkali metal salts (for example sodium or potassium salts), alkaline earth metal salts, transition metal salts, ammonium or substituted ammonium salts.

Specified fluoropyridine compounds, useful as active ingredients in the herbicidal compositions of the invention, are listed in Table 1 below. These compounds include compounds possessing either total or selective activity as herbicies.

TABLE 1

| Compound No. | Formula | Melting Point ° C |
|---|---|---|
| 1 | 3,5-dichloro-2,6-difluoro-4-hydroxypyridine | 100–102 |
| 2 | 3-chloro-2,5,6-trifluoro-4-hydroxypyridine | 122–124 |
| 3 | 2,3,5,6-tetrafluoro-4-hydroxypyridine | 96–96.5 |
| 4 | 3,5-dichloro-2,4-difluoro-6-hydroxypyridine | 151–153 |
| 5 | 3,4,5-trichloro-2-fluoro-6-hydroxypyridine | 172–176 |
| 6 | 4-acetoxy-3,5-dichloro-2,6-difluoropyridine | 55–56 |
| 7 | 4-benzoyloxy-3,5-dichloro-2,6-difluoropyridine | 96–97 |
| 8 | 3,5-dichloro-2,6-difluoro-4-pivaloyloxypyridine | 63–64 |
| 9 | 3,5-dichloro-2,6-difluoro-4-(4-methoxyphenoxycarbonyloxy)pyridine | 69.5–70 |

TABLE 1-continued

| Compound No. | Formula | Melting Point or boiling point ° C |
|---|---|---|
| 10 | 3-OSO2-C6H4-CH3(4), 2,6-diCl, 4,6-diF pyridine | 101–102 |
| 11 | 3-OCOC11H23(n), 2,6-diCl, 4,6-diF pyridine | 44–45 |
| 12 | 3-SCOCH3, 2,6-diCl, 4,6-diF pyridine | 111.5–112.5 |
| 13 | 3-SCOCH3, 2-Cl, 4,5,6-triF pyridine | 69–70 |
| 14 | 3-S·CO·CH2·CH3, 2-Cl, 4,5,6-triF pyridine | 47–48 |
| 15 | 3-S·SO2-C6H4-CH3(4), 2-Cl, 4,5,6-triF pyridine | 118–119 |
| 16 | 3-OK, 2,6-diCl, 4,6-diF pyridine | not below 300 |
| 17 | 4-ONa, 2,3,5,6-tetraF pyridine | not below 300 |
| 18 | 4-OK, 2,3,5,6-tetraF pyridine | M.p. not below 300 |
| 19 | 4-OCOCH3, 2,3,5,6-tetraF pyridine | M.p. 25 |
| 20 | 4-OCOC6H5, 2,3,5,6-tetraF pyridine | M.p. 57 |
| 21 | 4-OSO2CH3, 2,3,5,6-tetraF pyridine | B.p. 62–64/0.05 mm |
| 22 | 4-OSO2C6H13n, 2,3,5,6-tetraF pyridine | B.p. 98–100/0.06 mm |
| 23 | 4-OSO2C6H5, 2,3,5,6-tetraF pyridine | M.p. 51–53 |
| 24 | 4-OSO2-C6H4-NO2(2), 2,3,5,6-tetraF pyridine | M.p. 75–76 |
| 25 | 4-OSO2-C6H4-Cl(4), 2,3,5,6-tetraF pyridine | M.p. 68–69 |
| 26 | 4-OSO2-C6H4-OCH3(4), 2,3,5,6-tetraF pyridine | B.p. 134–136/0.05 mm |
| 27 | 4-OSO2-C6F5, 2,3,5,6-tetraF pyridine | B.p. 92–94/0.1 mm |

The invention also consists in new fluoropyridine compounds having the formula:

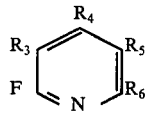

where $R_3$ and $R_5$, which may be the same or different, are atoms of fluorine or chlorine and either a. $R_6$ is an atom of fluorine or chlorine and $R_4$ is an —S.CO.X, —O.X, —0.SO$_2$.X, or S.SO$_2$.X group where X is an unsubstituted, or substituted, alkyl or aryl radical, or b. $R_6$ is an hydroxyl group and $R_4$ is an atom of chlorine; or a salt thereof.

The invention particularly consists in new fluoropyridine compounds of the general formula set out in the preceding paragraph and wherein $R_6$ is an atom of fluorine and $R_4$ is an —S.CO.X, —O.CO.X, —O.SO$_2$.X or —S.SO$_2$.X group where X is an alkyl group containing from 1 to 12 carbon atoms, a phenyl radical, or an alkyl-, alkoxy-, nitro- or halo- substituted phenyl radical.

The salt may be derived from a wide variety of organic or inoganic bases. It is preferred that the salt be a water-soluble salt. Suitable salts include alkali metal salts (for example sodium or potassium salts), alkaline earth metal salts, transition metal salts, ammonium or substituted ammonium salts.

These compounds may be made from a pyridine derivative containing five halogen atoms (chlorine or fluorine) as starting material, by reaction of the pentahalopyridine with a nucleophilic reagent which replaces the halogen atom in the 4 or 6 position in the pyridine ring by the appropriate $R_4$ or $R_6$ group. The starting material may be in particular 3-chloro-2,4,5,6-tetra-fluoropyridine, 2,3,4,5-tetrachloro-6-fluoropyridine, 2,6-difluoro-3,4,5,-trichloropyridine, or 2,4,6-trifluoro-3,5-dichloropyridine. The choice of starting material is governed by whether or not $R_4$ or $R_6$ is to be chlorine or fluorine in the required product, and the starting material employed should therefore contain chlorine and fluorine atoms as substituents in those positions of the ring in which they are required in the product. Either chlorine or fluorine atoms may be displaced by the nucleophilic reagent.

Suitable nucleophilic reagents include alkali metal hydroxides, in particular sodium or potassium hydroxide, and thioacids.

Alternatively the appropriate 4-hydroxy compound or a salt thereof, may be used as starting material for the preparation of compounds in which $R_4$ is an —O.CO.X, or —O.SO$_2$.X group and for this purpose is reacted with the appropriate acid chloride. An alternative method for preparing the compounds in which $R_4$ is a —S.CO.X group or —S.SO$_2$.X group comprises reacting a mercapto-halopyridine or a metal salt thereof with an acyl chloride.

The compositions of this invention may be used for agricultural and horticultural purposes and the type of composition used in any instance will depend upon the particular purpose for which it is to be used. Thus the composition can be in the form of a powder in which a minor amount of the active ingredient is in admixture with a major amount of solid diluent. Suitable solid diluents include powdered kaolin, Fuller's earth, gypsum, chalk, Hewitt's earth and china clay. In general liquid compositions are preferred because they can be applied more conveniently.

Liquid compositions usually comprise a solution or dispersion of the active ingredient in water containing a surface active agent. In dispersions, the active ingredient can be present in the composition as solid particles or as droplets of a solution of the active ingredient in a water insoluble solvent. Surface active agents which can be used include condensation products of ethylene oxide with various substances, for example with alkylated phenols, such as octyl phenol and nonyl phenol; sorbitan monolaurate, oleyl alcohol, cetyl alcohol and propylene oxide polymer. Other agents which are also satisfactory include calcium dodecyl benzene sulphonate, calcium lignosulphonate, sodium lignosulphonate and ammonium lignosulphonate. One method of making a liquid composition comprises dissolving the active ingredient in an organic solvent and then agitating the solution with water containing the surface active agent. A preferred method comprises first dissolving both the surface active agent and the active ingredient in the solvent and then agitating the solution with water.

The amounts of the active ingredient which may be used in the composition can vary widely depending upon the ingredient which is to be used and which weeds or their seeds are to be combatted. In general, however, compositions containing from 2.0 to 0.1% by weight give good results although larger or smaller quantities may sometimes be desirable.

The compositions are conveniently made available by a supplier in the form of a concentrate which is a composition containing a high proportion of the active ingredient and which therefore is generally required to be diluted, usually with water, before application. The concentrates can contain from 5 to 80% by weight of the active ingredient although for practical purposes from 20 to 70% by weight is usually preferred.

An especially satisfactory form of concentrate comprises the active ingredient which has been finely divided and which has been dispersed in water in the presence of a surface active agent and a suspending agent. Suspending agents which are preferred are those which impart thixotropic properties to, and increase viscosity of, the concentrate, for example water soluble hydrated colloidal mineral silicates and organic substances of a high molecular weight known in the art relating to the formulation of herbicides. Suspending agents which are very satisfactory include montmorillonite, beidellite, nontronite, hectorite, saponite, saucorite, cellulose derivaties and polyvinyl alcohol. Especially satisfactory concentrates contain bentonite as a suspending agent. Another form of concentrate comprises a "wettable" powder, that is to say a mixture of the active ingredient which has been finely divided and mixed with a solid surface active agent with or without an additional solid diluent. When agitated with water the surface active agent dissolves and promotes the dispersion of the finely divided active ingredient.

The compositions can be used for combating a wide range of broad and narrow leafed weeds.

If desired the compositions of the invention can incorporate additional active ingredients, more particularly other weed-killing substances having either residual or non-residual weed-killing properties. Of the latter class the bipyridyl weed-killers known as paraquat and diquat are each particularly suitable as an additional active ingredient in view of the potentiation effect between each of these substances and the fluoropyridine compounds contained in the compositions of this invention.

The compositions can be used as pre-emergent herbicides in which connection they are applied to the soil containing weed seeds and persist in the soil for a sufficient time either to kill the seeds or to kill or damage the seedlings they form. The compositions can also be used in a conventional way as post-emergent herbicides in which connection they are applied to the established weeds. A composition which can be used to good effect for one purpose may not always possess sufficient activity for the other and therefore some simple testing may be required to determine which compositions should be used against a particular weed population in order to obtain the best results.

In a further aspect, therefore, the invention consists in a method of combating unwanted vegetation which comprises applying to the locus of the unwanted vegetation or of seeds thereof a composition according to the invention.

In addition to their use as herbicides the compositions and compounds of this invention also exhibit pesticidal, fungicidal, nematicidal and plant growth regulating activity.

The invention is illustrated by the following examples:

EXAMPLE 1

This example illustrates a wettable powder comprising:

|  | % wt. |
|---|---|
| Compound 1 (of Table 1) | 50% |
| Calcium lignosulphonate | 10% |
| China clay | 40% |
|  | 100% |

Prior to use the composition is agitated with sufficient water to enable an aqueous dispersion containing 0.5% by weight of the compound to be formed.

EXAMPLE 2

This example illustrates a concentrate which is in the form of a paste and which forms a stable aqueous dispersion of the active ingredient when agitated with water

|  | % wt. |
|---|---|
| Compound 13 (of Table 1) | 20% |
| "DISPERSOL" T | 5% |
| Bentonite | 1% |
| Water | 74% |
|  | 100% |

"DISPERSOL"T is the trade name for the surface active agent.

EXAMPLE 3

This example illustrates the preparation of 2-fluoro-3,4,5-trichloro-6-hydroxpyridine (thought to exist in the form of 3,4,5-trichloro-6-fluoro-2-pyridone).

A solution of 3,4,5-trichlorodifluoropyridine (21.8 g.) in dioxan (220 ml.) was refluxed with a solution of sodium hydroxide (8 g.) in water (40 ml.). After 2 hours a further 8 g. of sodium hydroxide in water (40 ml.) was added (4 molar equivalents of sodium hydroxide in toto). After a further 2 hours, water was added to produce a homogeneous solution which was acidified to precipitate the product (17.6 g., m.p. 170°–4°). After initial purification by charcoal and silica gel column, crystallisation from benzene gave 3,4,5-trichloro-6-fluoro-2-pyridone, m.p. 172°–6°(11.8 g.), having a pale yellow colour. After vacuum sublimation at 100°–120°, the white microcrystals melted at 173°–4° (10.65 g/.).

Analysis: Found C, 27.4; H, 0.6; Cl, 49.2; N, 6.5; F, 8.65% $C_5HCl_3FNO$ requires C, 27.75; H, 0.5; Cl, 49.15; N, 6.5; F, 8.8%. Gas liquid chromatography showed a single component. The infra red spectrum showed a marked resemblance to that of 3,4,5,6-tetrachloro-2-pyridone, with a carbonyl frequency at 1618 cm$^{-1}$. Ultraviolet spectrum showed λ (max) 291 mμ (ε7600) in hexane and 312 mμ(ε7340) in $^{N/}10$ NaOH. The mass spectrum confirmed the mass number (215) and the presence of three chlorine atoms, and the fragmentation pattern (initial loss of CO) strongly suggested the pyridone tautomer rather than the pyridinol.

EXAMPLE 4

This example illustrates the preparation of 2,6-difluoro-3,5-dichloro-4-acetoxypyridine.

A solution of 5.9 g. of the potassium salt of 2,6-difluoro-3,5-dichloro-4-hydroxypyridine in 20 ml. of dry acetone was treated with a solution of 2.44 g. (2.2 ml.) acetyl chloride dissolved in 1 ml. of dry acetone, at such a rate that the temperature of the reaction mixture did not exceed 25° C. The mixture was then refluxed for 3 hours, cooled and filtered. Evaporation of the filtrate, and recrystallization of the residue from petroleum ether yielded white crystals m.p. 55°–6°.

Analysis: $C_7H_3O_2NCl_2F_2$ requires C, 34.75; H, 1.24; N, 5.79; Found: C, 35.00; H, 1.80; N, 5.96.

EXAMPLE 5

This examples illustrates the preparation of 3-chloro-4-propionytrifluoropyridine.

A stirred solution of 10.0 g. of the potassium salt of 3-chloro-4-mercapto-trifluoropyridine dissolved in 25 ml. of dry acetone is treated with a solution of 5.7 g. of propionyl chloride dissolved in 25 ml. of dry acetone, at such a rate that the temperature does not exceed 25°. The reaction mixture is then refluxed for 4 hours and filtered whilst hot. Removal of the solvent followed by recrystallisation from dry petroleum ether gives white needles m.p. 47.8°.

EXAMPLE 6

This example illustrate the preparation of 3-chloro-4-acetylthio-2,5,6-trifluoropyridine.

A solution of 9.27 g. 3-chloro-2,4,5,6-tetrafluoro-pyridine dissolved in 20 ml. of dry dioxan, in which 2.91 g. of anhydrous sodium carbonate has been suspended is cooled to 5° C. A solution of 4.18 g. of thioacetic acid dissolved in 10 ml. of dry dioxan is then added, while the reaction mixture is stirred at such a rate that the temperature of the reaction mixture, kept cold by immersion in ice-water, does not rise above 10° C. When the addition is complete the mixture is allowed to warm to room temperature and is then refluxed for ½ hour. The solvent is removed and the residue extracted with dry chloroform. Evaporation of the chloroform, followed by recrystallization of the residue yields white needles m.p. 69°–70°;

Analysis: $C_7H_3ONClF_3S$ requires C, 34,78; H, 1.24; S, 13.25; Found C, 35.40; H, 1.60; S, 13.13. The infra red spectrum, n.m.r. F$^{19}$ spectrum and mass spectrum all supported the assigned structure.

EXAMPLE 7

This example illustrates the preparation of the potassium salt of 2,6-difluoro-3,5-dichloro-4-hydroxpyridine.

A solution of 25 g. of 2,6-difluoro-3,5-dichloro-4-hydroxypyridine dissolved in 200 ml. of acetone was treated with 17.25 g. of solid, anhydrous potassium carbonate. When the effervescence had diminished, the mixture was warmed on the steam-bath for 5 minutes and then filtered. After removal of the solvent, the salt was obtained as a white solid, m.p. not less than 300° C.

EXAMPLE 8

This example illustrates the preparation of the potassium and sodium salts of 4-hydroxy-tetrafluoropyridine.

A solution of 4-hydroxy-tetrafluoropyridine (12.5% w/v) in acetone was stirred with solid anhydrous potassium carbonate (2 equivalents). After the effervescence had diminished, the mixture was warmed on the steam bath for 5 minutes and then filtered. Evaporation of the filtrate gave the potassium salt as a white solid.

The sodium salt was obtained as a white solid by following the above procedure using sodium carbonate in place of potassium carbonate.

EXAMPLE 9

This example illustrates the preparation of 4-p-chlorobenzenesulphonyloxytetrafluoropyridine, having the formula:

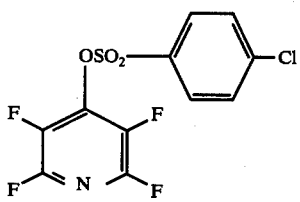

A solution of the potassium salt of 4-hydroxytetrafluoropyridine (30% w/v) in dry acetone was treated with a solution (25% w/v) of p-chlorobenzenesulphonyl chloride (1 molar proportion) in dry acetone at such a rate that the temperature of the reaction mixture did not exceed 25° C. The mixture was then heated under reflux for 3 hours, cooled amd filtered. Evaporation of the filtrate and recrystallisation of the residue gave white crystals m.p. 68°–69°.

EXAMPLE 10

This example illustrates the preparation of further esters of 4-hydroxytetrafluoropyridine. These were prepared by the procedure of Example 9, using the appropriate acid chloride. The compounds so prepared are set out in Table 2 below, in which the symbol Q indicates the group

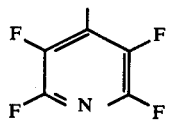

Table 2

| Compound No. | Structure | Melting point or boiling point ° C |
|---|---|---|
| 1 | QOSO$_2$—⟨⟩—OCH$_3$ | B.p. 134–136° /0.05 mm |
| 2 | QOSO$_2$CH$_3$ | B.p. 62–64° /0.05 mm |
| 3 | QOSO$_2$—⟨⟩ | M.p. 51–53° |
| 4 | QOCO—⟨⟩ | M.p. 57° |
| 5 | QOCOCH$_3$ | M.p. 25° |
| 6 | QOSO$_2$—(C$_6$F$_5$) | B.p. 92–94° /0.1 mm |
| 7 | QOSO$_2$—⟨NO$_2$⟩ | M.p. 75–76° |
| 8 | QOSO$_2$C$_6$H$_{13}$n | B.p. 98–100° /0.06 mm |

EXAMPLE 11

This example describes the preparation of herbicidal compositions containing different fluoro pyridines and tests to illustrate the phytotoxic properties of the compositions. In some of the tests plants were employed which are not normally regarded as weeds but which are useful, nevertheless, for measuring phytotoxic activity.

The compositions were made by finely grinding each of the fluoro pyridines mentioned below and then dispersing 1% by weight of the powdered material in water containing 0.1% by weight of a surface active agent which is sold under the trade name "AGRAL" 90; "AGRAL" being a registered Trade Mark. In order to facilitate grinding of the active ingredients a small proportion of the surface agent present in the resulting compositions was added during the grinding operation.

The fluoro pyridines used in the compositions were as follows:

| Compound No. (of Table I) | Name |
|---|---|
| 1 | 2,6-difluoro-3,5-dichloro-4-hydroxy pyridine |
| 5 | 2-fluoro-3,4,5-trichloro-6-hydroxy pyridine |

The pre- and post-emergent herbicidal activity of the compositions was then tested in the following way.

In the test for pre-emergent herbicidal activity flower pots were filled with compost into which grooves were formed. The compost was then treated with the test solution and seeds were then sown into the grooves which were then closed so as to cover the seeds with soil. After the elapse of twenty one days the number of any healthy seedlings which managed to develop was compared with the number growing in pots of soil which had not been treated with a test composition.

In the test for post-emergent herbicidal activity seeds were sown in flower pots and were allowed to mature into seedlings at the two leaf stage. The seedlings were then sprayed with a test composition and fourteen days were allowed to elapse. After this period the number of seedlings which had been damaged or destroyed was determined The results of the tests are summarized below in the tables. The figures shown in the first column under the name of each test plant represent the percentage of seeds which failed to mature into undamaged seedlings in the test for pre-emergent activity and the second column gives the percentage of seedlings damaged or destroyed in the test for post-emergent activity.

TABLE 3

| Compound | Barley | | Wheat | | Wild Oats | |
|---|---|---|---|---|---|---|
| No. | Pre | Post | Pre | Post | Pre | Post |
| 1 | 100 | 80 | 100 | 80 | 100 | 100 |
| 5 | 80 | 40 | 60 | 20 | 40 | 20 |

What is claimed is:

1. A method of combating unwanted vegetation which comprises applying to the locus of the unwanted vegetation or of seeds thereof a herbicidally effective amount of a fluoropyridine compound of the formula:

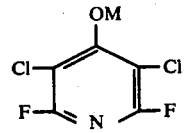

wherein M is selected from the group consisting of hydrogen, alkali metals, alkaline earth metals and ammonium ion.

2. The method of claim 1 wherein the active ingredient is 3,5-dichloro-2,6-difluoro-4-hydroxy-pyridine.

* * * * *